(12) United States Patent
Maurer et al.

(10) Patent No.: US 8,206,651 B2
(45) Date of Patent: Jun. 26, 2012

(54) SYSTEM FOR DETECTION OF BIOLOGICAL AGENTS

(75) Inventors: Scott M. Maurer, Haymarket, VA (US);
Ryan C. Brewer, Bristow, VA (US);
Larry D. Jackson, Manassas, VA (US);
Kevin J. Kofler, Bristow, VA (US);
Mark J. Derksen, Bristow, VA (US)

(73) Assignee: Lockheed Martin Corporation, Bethesda, MD (US)

( * ) Notice: Subject to any disclaimer, the term of this patent is extended or adjusted under 35 U.S.C. 154(b) by 2010 days.

(21) Appl. No.: 10/891,644

(22) Filed: Jul. 15, 2004

(65) Prior Publication Data
US 2006/0014236 A1    Jan. 19, 2006

(51) Int. Cl.
*G01N 21/64* (2006.01)
*G01N 33/483* (2006.01)

(52) U.S. Cl. ............... 422/82.08; 422/66; 422/82.05; 435/287.1; 73/28.01; 73/31.01

(58) Field of Classification Search ............... 378/45; 422/66, 82.05, 82.08; 435/287.1; 73/28.01, 73/31.01
See application file for complete search history.

(56) References Cited

U.S. PATENT DOCUMENTS

| | | | |
|---|---|---|---|
| 4,113,434 A * | 9/1978 | Tanaka et al. | 73/863.55 |
| 4,530,250 A * | 7/1985 | Gay et al. | 73/863.12 |
| 4,551,848 A * | 11/1985 | Greenwood-Smith | 378/45 |
| 5,034,038 A * | 7/1991 | Olson | 96/228 |
| 5,234,739 A * | 8/1993 | Tanaru et al. | 428/131 |
| 5,710,628 A * | 1/1998 | Waterhouse et al. | 356/344 |
| 6,458,547 B1 * | 10/2002 | Bryan et al. | 435/7.1 |
| 2002/0113136 A1 * | 8/2002 | Talley et al. | 239/1 |
| 2003/0025086 A1 * | 2/2003 | Stroka | 250/461.1 |
| 2004/0021860 A1 * | 2/2004 | Gardner et al. | 356/301 |

* cited by examiner

*Primary Examiner* — In Suk Bullock
*Assistant Examiner* — Paul Hyun
(74) *Attorney, Agent, or Firm* — DeMont & Breyer, LLC

(57) ABSTRACT

The illustrative embodiment of the present invention is a system and a method for the detection and limited identification of biological agents. The system is small, light weight, requires little power to operate and uses few consumables. The system can be configured for use in either stationary or mobile applications. The system incorporates elements that enable it to obtain an air sample, extract particulates from the air sample, exposes the particulates to electromagnetic radiation, and monitor for fluorescent emissions. To the extent that fluorescent emissions are detected and exceed a predetermined value, an alarm is triggered.

12 Claims, 7 Drawing Sheets

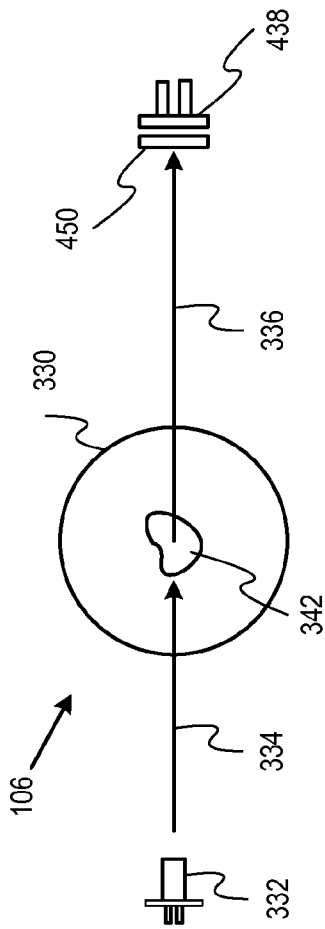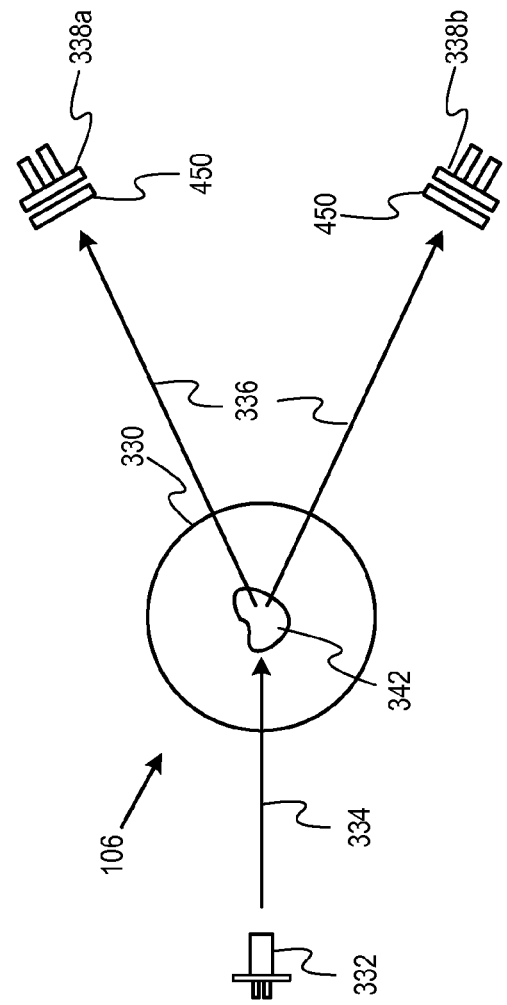
FIG. 4
FIG. 5

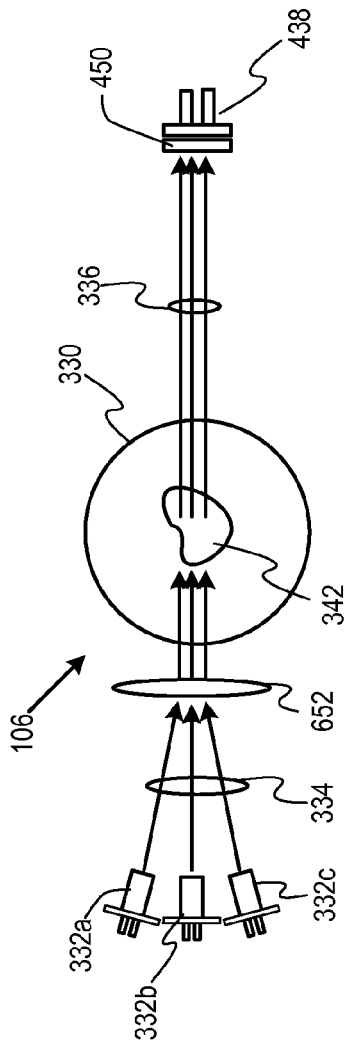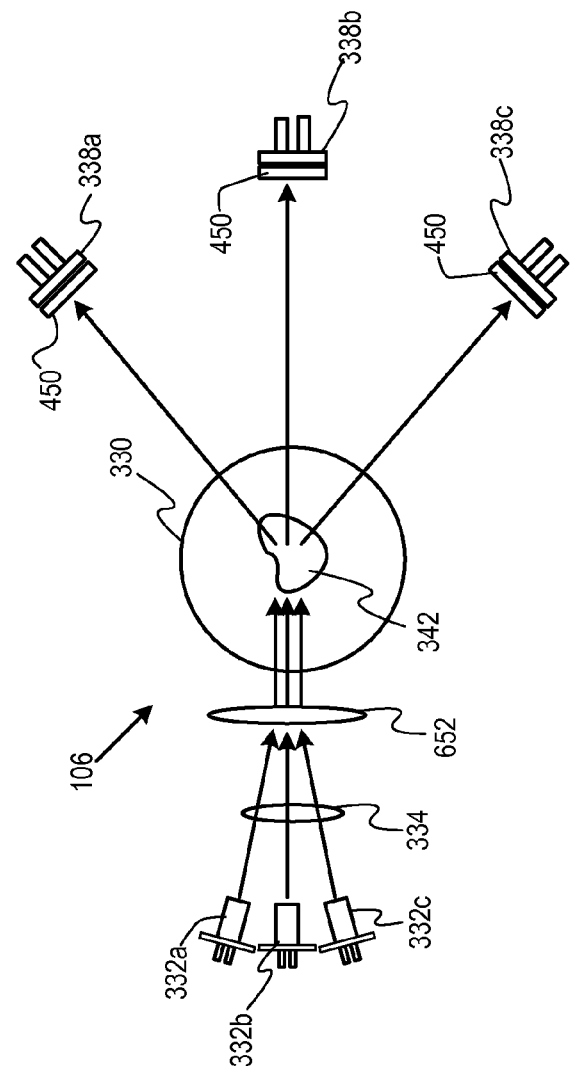

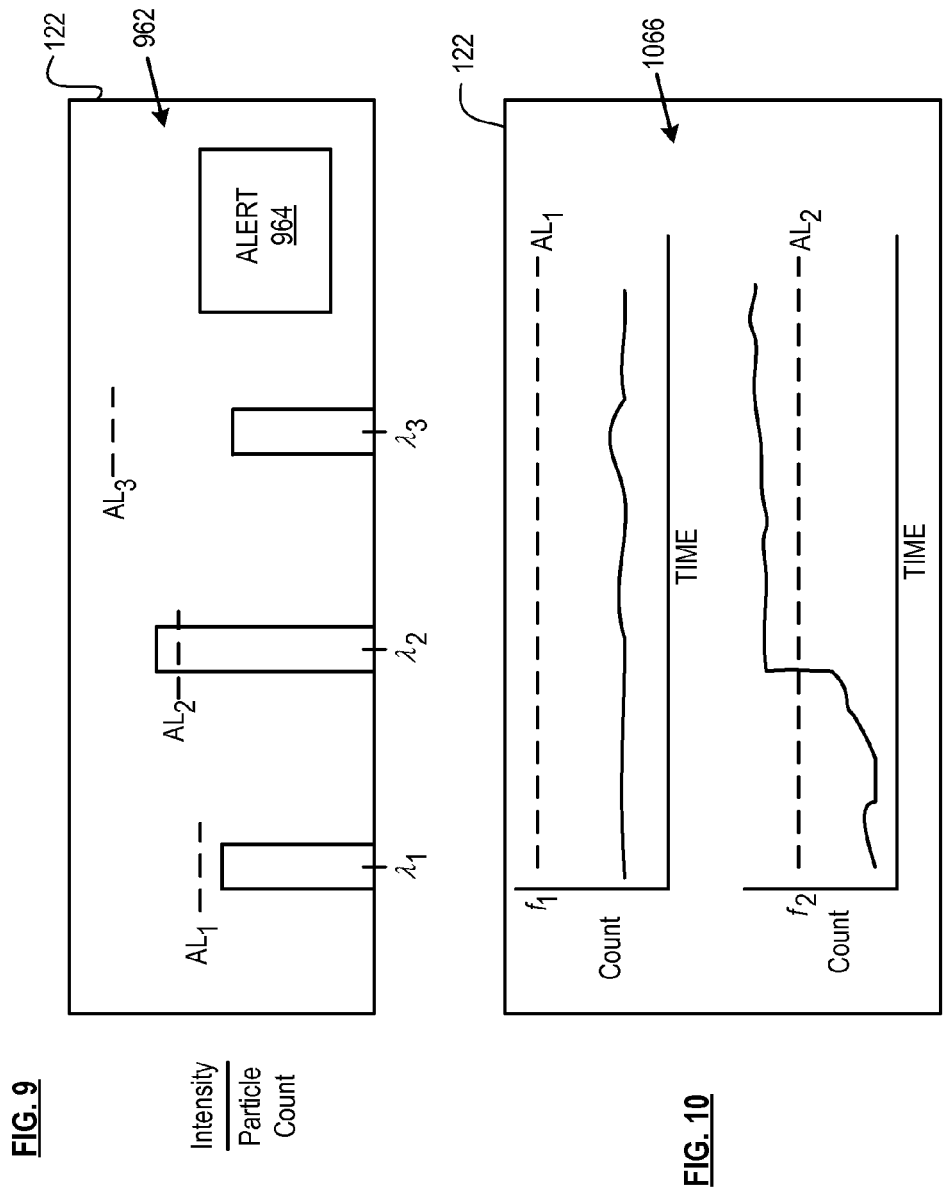

SYSTEM FOR DETECTION OF BIOLOGICAL AGENTS

STATEMENT OF RELATED CASES

This case is related to co-pending U.S. patent application Ser. Nos. 10/891,805, 10/891,812, 10/891,573, and 10/891,638, which were filed on even date herewith and are incorporated herein by reference.

BACKGROUND OF THE INVENTION

Biological warfare is the intentional use of microorganisms and toxins of microbial, plant or animal origin to produce diseases and/or death in humans, livestock and crops. To terrorists, biological warfare is attractive because bio-weapons have relatively low production cost, it is relatively easy to obtain a wide variety of disease-producing biological agents, bio-weapons are non-detectable by routine security systems, and bio-weapons are easily transportable.

Unlike relatively mature radiation- and chemical-detection technologies, early-warning technology for biological agents is in its infancy. Most known bio-detection systems are "flow-through," wherein individual particles that are contained in a flowing stream (e.g., air, etc.) are interrogated in an optical cell. Interrogation is typically performed using high-power lasers. The flowing stream, and hence the particles, have an extremely low residence time in the optical cell. As a consequence, the laser samples only a portion of the stream, must be relatively high power to provide an appropriate signal-to-noise ratio, and must be operating constantly to ensure detection.

Furthermore, some bio-detection systems use consumables, such as buffered saline solutions, antibodies, assay strips, reagent solutions, cleansing solution and antibodies. Most of these consumables have a specific shelf life, which creates a logistical burden. Furthermore, these consumables are typically unable to withstand demanding thermal requirements in theater. Also, many current bio-detection systems are large, heavy, and consume large amounts of power.

The drawbacks of prior-art bio-detection systems, as described above, significantly limit their usefulness in the field.

SUMMARY

The illustrative embodiment of the present invention is a sensing system and method for the detection and limited identification of biological agents. Unlike many prior-art bio-detection systems, the sensing system is small, light weight, requires little power to operate and uses few consumables. The system can be configured for use in either stationary or mobile applications.

The principle of operation for the sensing system is that many biological agents "fluoresce" when excited by radiation that has an appropriate wavelength, which is typically within or near the ultraviolet range. "Fluorescence" is the radiation that is emitted from a biological agent (or other substances) when it is excited as described above. What occurs at a molecular level is that the substance absorbs a photon of electromagnetic radiation, which causes an electron in the substance to move from a low energy state to a higher one. When the electron returns to a lower energy state, a photon is emitted. This photon is fluorescent radiation.

Since many types of biological agents fluoresce under ultraviolet light, the detection of fluorescent emissions from a sample that has been exposed to radiation having a wavelength in or near the ultraviolet range indicates that biological agents might be present. This is the detection function of the sensing system; some embodiments of the sensing system also provide a limited identification function as well.

Regarding identification, different biological agents contain different fluorescing organic substances (e.g., differing in amount or type). As a consequence, the peak intensity of the fluorescence emissions and/or characteristic fluorescent spectra for these different biological agents will be different. This attribute, among any others, provides a basis for at least limited identification of biological agents.

Briefly, in a method in accordance with the illustrative embodiment:
- an air sample is obtained;
- particulates are extracted from the air sample;
- the particulates are exposed to electromagnetic radiation (typically in the ultraviolet to blue range of wavelengths); and
- the particulates are monitored for fluorescent emissions.

To the extent that fluorescent emissions are detected and exceed a predetermined value, it is indicative that a biological attack might be in progress or might have occurred. Characteristics of the fluorescent emissions (e.g., wavelength, intensity, etc.) can be used to identify a biological agent that has been detected by the system.

A sensing system in accordance with the illustrative embodiment comprises an interrogation cell, which has:
- A stationary-phase collection media for extracting and retaining particulates, including biological agents, from an air sample.
- A source of electromagnetic radiation for exposing particulates that have been retained in the collection media. If the retained particulates include biological agents, they will fluoresce when exposed to electromagnetic radiation having an appropriate wavelength. Wavelengths within a range of about 250 to about 500 nanometers are appropriate for causing fluorescence in many biological agents. In the illustrative embodiment, the source of electromagnetic radiation is one or more light-emitting diodes ("LEDs").
- A detector, such as a photodetector, for monitoring fluorescent emissions. The detector must be sensitive to the wavelengths of radiation at which biological agents fluoresce. The peak wavelength(s) of fluorescent emissions from biological agents of interest is typically in the range of about 300 to about 600 nanometers.

In addition to the interrogation cell, the sensing system also includes control/data-acquisition/data-processing circuitry. This circuitry is capable of implementing the following functions, among others:
- Controlling the operation of the source of electromagnetic radiation, including an ability to intermittently activate the source.
- Controlling the operation of the detector including activating the detector and acquiring data from the detector.
- Signal processing. A signal generated by the photodetector is processed to:
  - detect: determine if a biological agent is present in the air sample;
  - quantify: estimate the amount of biological agent present, if any;
  - assess: determine if the amount of a biological agent present is indicative of a biological attack or otherwise poses a risk to the health of the local population, livestock, etc.; and
  - identify: provide a limited identification of a biological agent that is detected.

BRIEF DESCRIPTION OF THE DRAWINGS

FIG. 4 depicts a first variation of the interrogation cell of FIG. 3.

FIG. 5 depicts a second variation of the interrogation cell of FIG. 3.

FIG. 7 depicts a fourth variation of the interrogation cell of FIG. 3.

FIG. 8 depicts a fifth variation of the interrogation cell of FIG. 3.

FIG. 9 depicts an illustrative graphical user interface for use in conjunction with the data-acquisition/data-processing electronics of FIG. 8 to present the results of data processing.

FIG. 10 depicts a variation of the graphical user interface depicted in FIG. 9.

DETAILED DESCRIPTION

The illustrative embodiment of the present invention is a sensing system and method for the detection and limited identification of biological agents. In some embodiments, the sensing system is very light and quite small, fitting in an enclosure that is about 1 inch×1 inch×2 inches. The system can be configured for use in either stationary or mobile applications.

Biological agents of interest here typically have a size that is in a range of hundreds of nanometers (e.g., for viruses, etc.) to a few microns (e.g., for bacteria, etc). Typical biological agents of interest include, for example, anthrax (1×2 micron), plague (0.5×1 micron), tularemia (0.5×1 micron), and small pox (200×250×250 nanometers). The illustrative embodiment of the present sensing system is capable of detecting particles in this size range. In some variations of the illustrative embodiment, the sensing system is configured to detect smaller biological agents, and in yet some additional variations, the sensing system is configured to detect larger biological agents.

Figure 1:
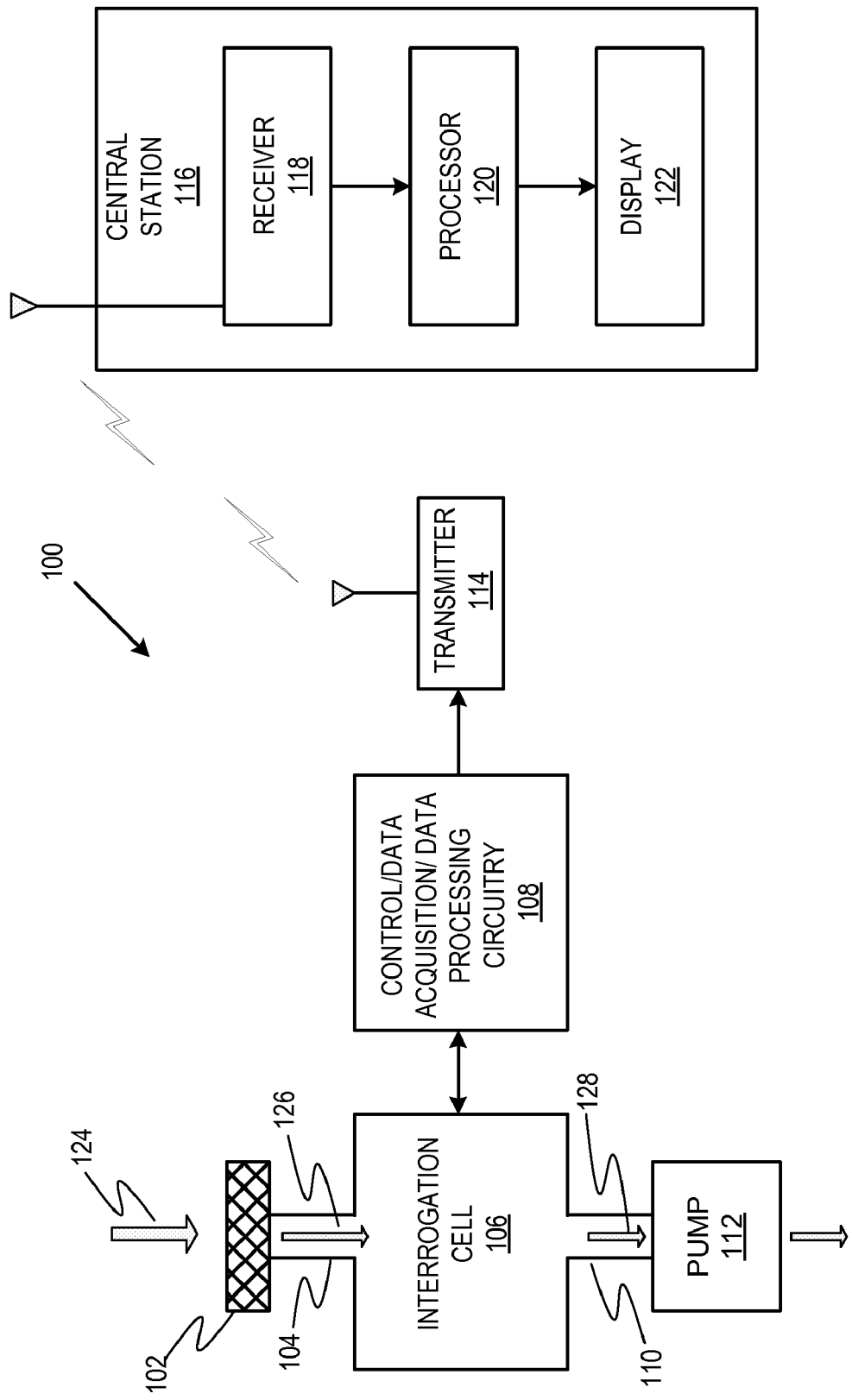
FIG. 1 depicts a sensing system for the detection of biological agents in accordance with the illustrative embodiment of the present invention.

FIG. 1 depicts sensing system 100 in accordance with the illustrative embodiment of the present invention. Sensing system 100 comprises interrogation cell 106, control/data acquisition/data processing circuitry 108, and central station 116, interrelated as shown.

A sample of air is obtained from the ambient environment for interrogation within interrogation cell 106. If sensing system 100 is stationary, then air is drawn through the sensing system by pump 112 or other similar device (e.g., a device that generates a suction flow, etc.). If the sensing system is moving (e.g., disposed on a vehicle, attached to a device that rotates the system, etc.), then pump 112 might not be necessary as a function of the speed at which sensing system 100 is moved.

In the illustrative embodiment, the sample of air, identified as flow 124 in FIG. 1, is filtered before it enters interrogation cell 106. In the illustrative embodiment, filtration is performed by filter 102, which is disposed upstream of cell inlet line 104.

Filter 102 prevents large particulate matter from entering interrogation cell 106. If large particulates were to enter interrogation cell 106, they might clog the interrogation cell, thereby shortening run time. In some embodiments, filter 102 filters particulate matter that is larger than about 50 microns. At this size, filter 102 will trap large dust particles, insects, and the like. Since, as described above, most biological agents of interest are much smaller than 50 microns, they will readily pass filter 102 and enter interrogation cell 106.

Filter elements suitable for use in the illustrative embodiment as filter 102 have a 50-micron pore structure and include, without limitation:

glass micro-fiber paper anodized aluminum
Teflon®-based materials stainless steel polymers/plastics.

At least some of these filter elements are available from Donaldson Company of Minneapolis, Minn.; the other elements are available from any of a variety of commercial suppliers.

As an alternative to filter 102, a micro virtual impactor concentrator (micro-VIC®) can be used. The micro-VIC®, which is available from MesoSystems Technology, Inc. of Albuquerque, N. Mex., utilizes inertial effects to discharge and separate larger particulates from relatively smaller biological agents. Another alternative to a filter is a rotating-arm impactor.

Filtered flow 126 of air is conducted via cell inlet line 104 to interrogation cell 106. As described more fully later in this specification, particulates are removed from filtered flow 126 and interrogated in the interrogation cell. After passing through interrogation cell 106, substantially particulate-free flow 128 of air is expelled from sensing system 100 via cell outlet line 110.

The operation of interrogation cell 106 is controlled by control/data acquisition/data processing circuitry 108. Information that is obtained from the interrogation of the particulates is transmitted to station 116, which, in the illustrative embodiment, is remote from interrogation cell 106. In the illustrative embodiment, transmission is performed wirelessly via transmitter 114. The transmitted information is received by receiver 118, is processed as required in processor 120, and is displayed on display 122. In some alternative embodiments, control/data acquisition/data processing circuitry 108 is wired to station 116.

Figure 2:
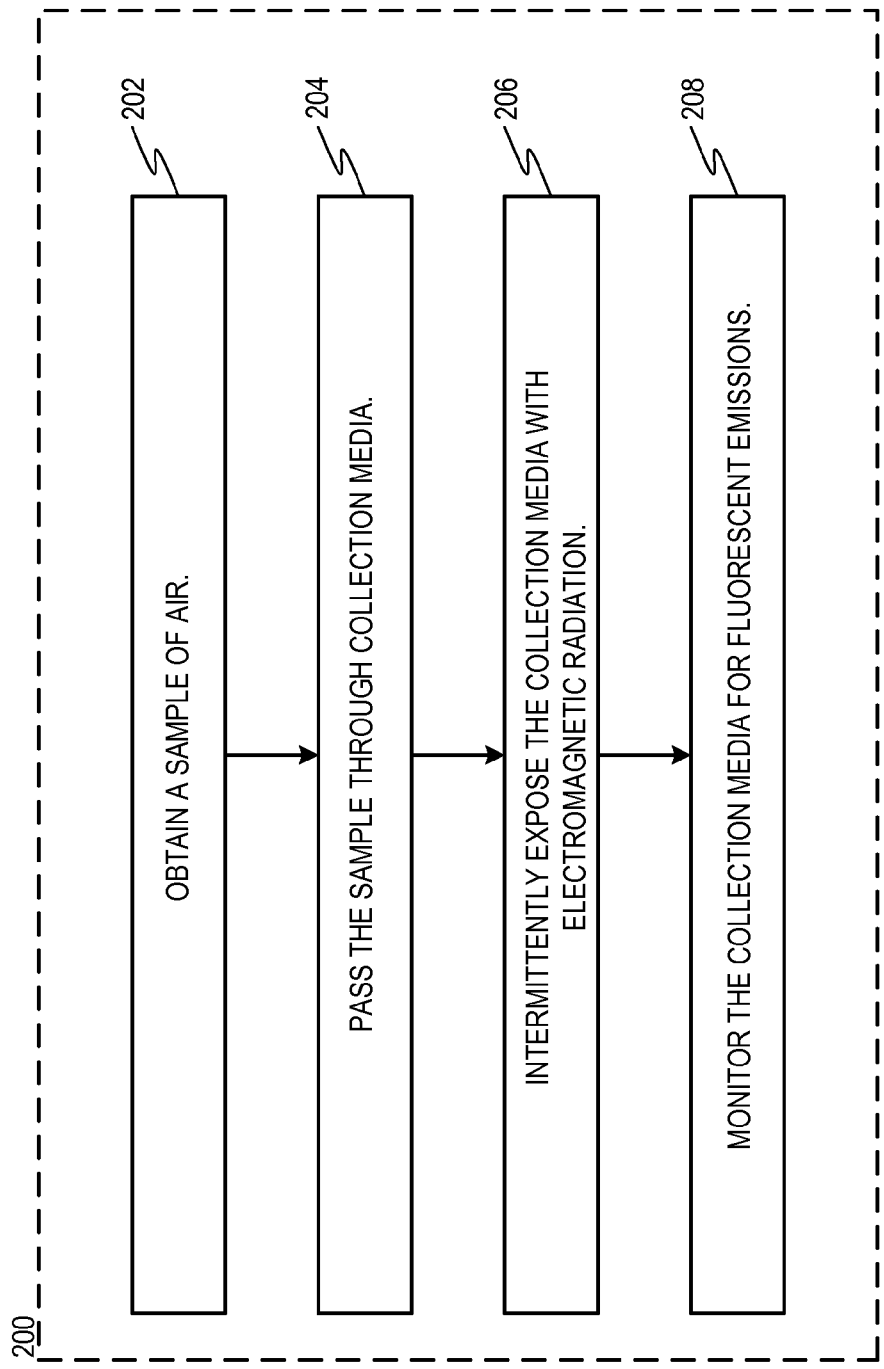
FIG. 2 depicts a method for the detection of biological agents in accordance with the illustrative embodiment of the present invention.

Having provided an overview of sensing system 100, description of the operation and structure of interrogation cell 106 is now provided. The description proceeds with reference to FIG. 2, which depicts method 200 for detection of biological agents, and FIG. 3, which depicts the structure of interrogation cell 106.

The operations of method 200 include:
  obtaining a sample of air (operation 202);
  passing the sample of air through collection media, wherein the collection media is capable of retaining particulates that are contained in the sample of air (operation 204);
  exposing the collection media to electromagnetic radiation (operation 206); and
  monitoring the collection media for fluorescent emissions (operation 208).

Operation 202 of method 200 recites "obtaining a sample of air." A purpose of operation 202 is to provide a sample of air for interrogation by interrogation cell 106.

Operation 204 of method 200 recites "passing the sample through collection media, wherein the collection media is capable of retaining particles contained in the sample." A purpose of operation 204 is to extract any biological agents that might be contained within the air sample (i.e., filtered air sample 126) so that they can be interrogated.

Figure 3:
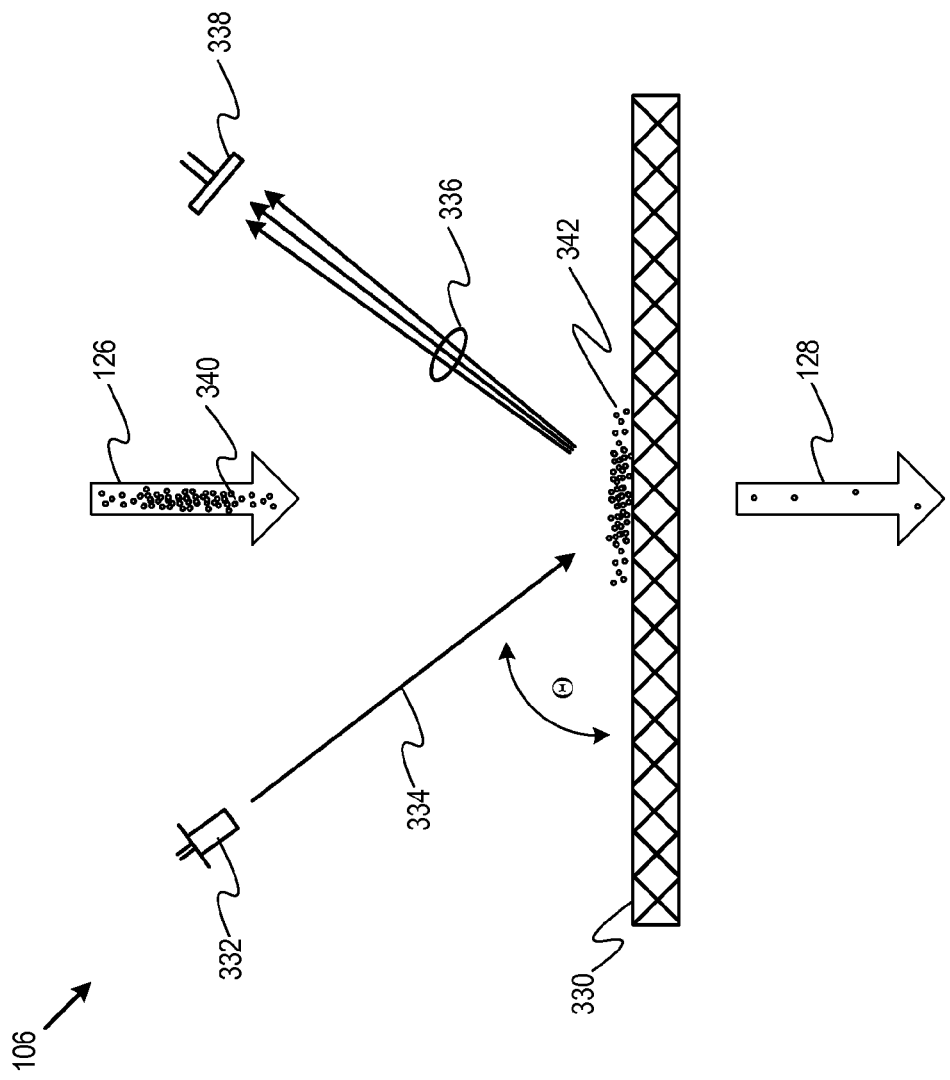
FIG. 3 depicts an interrogation cell of the sensing system of FIG. 1.

Referring now to FIG. 3, filtered air flow 126 is directed to stationary-phase collection media 330. The collection media comprises a stationary phase that is physically adapted to trap at least about 99 percent of particulates 340 that remain in filtered air flow 126 and have a size in the range of interest for biological agents (i.e., about 0.3-5 microns). Particulates that are retained by collection media 330 compose sample 342. Interrogation cell 106 can be provided with stationary-phase collection media 330 having a more definitive rating to the extent that it is intended to monitor a specific type of threat (i.e., a particular biological agent).

Stationary-phase collection media 330 suitable for use in conjunction with sensing system 100, as a function of the biological agents of interest, includes:

- HEPA/ULPA glass microfiber filtration media that is rated at >99.7% removal efficiency for particulates at 0.3 microns.
- PTFE/PFA/PFE (i.e., Teflon®-based) filtration media that is rated at >99% for particulates at 0.3 microns.
- Paper filtration media that is rated at >99% for particulates at 0.3 microns.
- Stainless Steel filtration media that is rated at >99% for particulates at 1 micron.
- Anodized Aluminum filtration media that is rated at >99% for particulates at 1 micron.
- Other types of filtration media such as plastics and other polymers that are rated at >99% for particulates at 0.3 microns.

As previously indicated, after passing through collection media 330, the now substantially particulate-free flow 128 of air is expelled to the ambient environment via cell outlet line 110.

In some embodiments, even those in which the sensing system 100 is mobile, an appropriately-valved pump is included in the system and used to reverse the flow of air through collection media 330. Reversing the flow of air removes at least some of the material (i.e., particulates 340) that has been retained by collection media 330. Reversing the flow in this manner might be necessary if the collection media becomes clogged. Alternatively, this technique can be used to establish a new interrogation baseline (e.g., for fluorescent emissions, etc.).

Operation 206 of method 200 recites "exposing the collection media to electromagnetic radiation." A purpose of this operation is to excite to fluorescence any biological agents that have been trapped by collection media 330.

With continuing reference to FIG. 3, interrogation cell 106 includes a source of electromagnetic radiation, which in the illustrative embodiment is LED 332. Electromagnetic radiation 334 generated by LED 332 is directed toward sample 342 on collection media 330. Since most biological agents of interest are excited by wavelengths between about 250 to 500 nanometers (i.e., the ultraviolet to blue range of wavelengths), the peak emission wavelength of LED 332 should be within this range. LEDs emit radiation over a range of wavelengths. Typically, one wavelength will contain more energy than any other single wavelength. That one wavelength is the "peak emission wavelength."

In some embodiments, LED 332 does not remain on continuously; rather, it is pulsed on and off. LED 332 is controlled for intermittent operation via control/data acquisition/data processing circuitry 108. In comparison with an always-on, laser-based system, the use of an LED, especially in a pulsed mode, consumes far less power. For example, when implemented without pump 112, the average power consumption of sensing system 100 is expected to be about 100 mW at 5V. The sensing system is adaptable for battery operation, as desired, at 6, 12 or 24 volts DC.

LED 332 is positioned at an out-of-plane angle θ relative to collection media 330. The angle θ is typically in the range of 0 to 90 degrees. More typically, angle θ lies between 45 to 60 degrees.

Operation 208 of method 200 recites "monitoring the collection media for fluorescent emissions." A purpose of this operation is to detect the presence of biological agents.

Referring again to FIG. 3, system 100 includes at least one photodetector 338 for monitoring fluorescent emissions 336 from any biological agents present in sample 342 on collection media 330. In the illustrative embodiment, the photodetector is a photodiode. Photodetector 338 must be sensitive to the wavelengths at which biological agents fluoresce. Most biological agents of interest fluoresce at wavelengths that are within the range of about 300 to about 600 nanometers. For example, tryptophan (an amino acid that is typically found in animal proteins or bacteria) has a peak emission at about 330 nanometers, NADH (usually associated with growth media and yeast grown products that are used for culturing organisms) has a peak at around 450 nanometers and flavins (again associated with growth media) have a peak at around 560 nanometers. As a consequence, photodetector 338 should be sensitive to wavelengths in this range.

Interrogation cell 106 can have a variety of configurations. A few of these configurations are described below and depicted in FIGS. 4-8.

Interrogation Cell Arrangement 1: Single LED and Single Photodetector

In some embodiments, such as the embodiment depicted in FIG. 3, interrogation cell 106 includes a single LED 332 and a single photodetector 338. As previously described, the LED should have a peak emission wavelength within the range of about 250 to about 500 nanometers and the photodetector should be sensitive to at least some wavelengths within the range of about 300 to 600 nanometers. This is perhaps the simplest configuration for interrogation cell 109.

Interrogation Cell Arrangement 2: Single LED and Photodetector Array or Multiple Individual Photodetectors In some embodiments, interrogation cell 106 comprises a single LED and a photodetector array (with respective peak emission wavelength and wavelength sensitivity as described for Arrangement 1). For example, FIG. 4 depicts LED 332 irradiating sample 342 on collection media 330. Electromagnetic radiation 334 emitted from LED 332 results in fluorescence 336 from biological agents that are contained within the sample. Fluorescence 336 is detected by photodetector array 438. Filter 450 captures the desired wavelengths for each photodetector element in the photodetector array.

Photodetector arrays suitable for use in conjunction with this embodiment are available from Texas Advanced Optoelectronic Solutions (TAOS), Inc. of Plano, Tex. and others. One such suitable array, for example, is available as TAOS TCS230, which is an RGB photodiode array comprising an 8×8 staggered arrangement of RGB and clear photodiodes.

In some other embodiments, interrogation cell 106 comprises a single LED (with peak emission wavelength as previously described) and two or more individual photodetectors (with wavelength sensitivity as previously described). For example, FIG. 5 depicts LED 332 irradiating sample 342 on collection media 330. Electromagnetic radiation 334 emitted from LED 332 results in fluorescence 336 from biological agents that are contained within the sample. Fluorescence 336 is detected by photodetectors 338*a* and 338*b*. Filters 450 captures the desired wavelengths for each of the individual photodetectors.

In some embodiments, linear variable filters ("LVF") are used in conjunction with photodetectors or photodetector arrays to filter the input for better discrimination. In other words, a linear variable filter can be used to create a notch filter with an adjustable center wavelength and an adjustable bandpass. Linear variable filters are available from OceanOptics, Inc. of Dunedin, Fla.

Interrogation Cell Arrangement 3: Multiple LEDs and Single Photodetector

Figure 6:
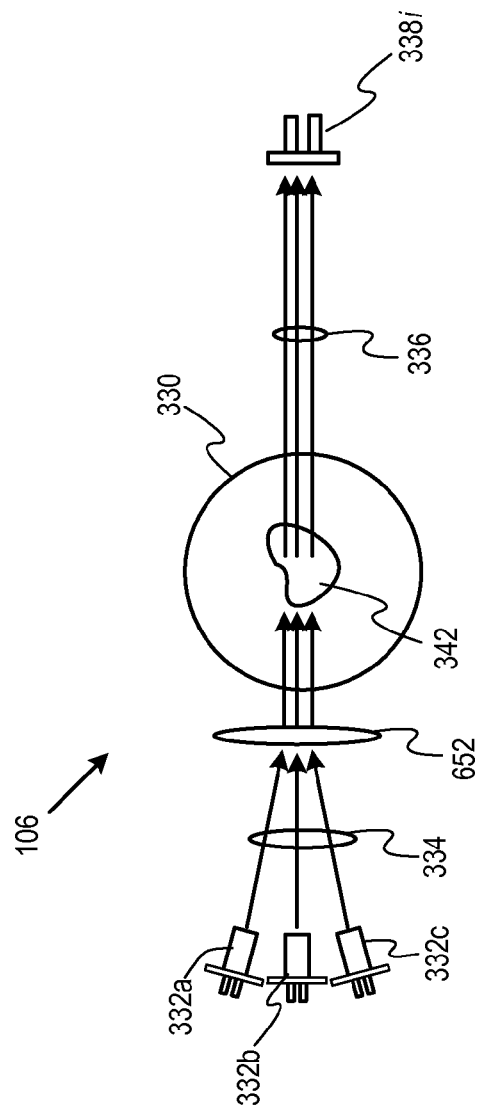
FIG. 6 depicts a third variation of the interrogation cell of FIG. 3.

In some embodiments, interrogation cell 106 includes two or more identical LEDs (i.e., same peak emission wavelength in the range described above). For example, FIG. 6 depicts three LEDs 332*a*, 332*b*, and 332*c* irradiating sample 342 on collection media 330. Electromagnetic radiation 334 emitted from the LEDs causes biological agents that are contained within the sample to fluoresce. Fluorescence 336 is captured by photodetector 338 (with wavelength sensitivity as previously described). The use of multiple LEDs, as in the embodiment depicted in FIG. 6, produces a more intense source of electromagnetic radiation than is possible from a single LED. Lens 652 is used to focus electromagnetic radiation 334 on sample 342.

Interrogation Cell Arrangement 4: Multiple LEDs and Photodetector Array or Multiple Individual Photodetectors In some embodiments, interrogation cell 106 includes multiple LEDs that operate at the same peak emission wavelength (in the range described above) and a photodetector array (with wavelength sensitivity as previously described). For example, FIG. 7 depicts LEDs 332*a*, 332*b*, and 332*c* irradiating sample 342 on collection media 330. Lens 652 is used to focus electromagnetic radiation 334 on sample 342. Electromagnetic radiation 334 emitted from the LEDs causes biological agents that are contained within the sample to fluoresce. Fluorescence 336 is detected by photodetector array 438. Filter 450 captures the desired wavelengths for each photodetector element in the photodetector array.

In some other embodiments, interrogation cell 106 comprises multiple LEDs that operate at the same peak emission wavelength (in the range described above) and two or more individual photodetectors (with wavelength sensitivity as described above). For example, FIG. 8 depicts LEDs 332*a*, 332*b*, and 332*c* irradiating sample 342 on collection media 330. Lens 652 is used to focus electromagnetic radiation 334 on sample 342. Electromagnetic radiation 334 emitted from the LEDs causes biological agents that are contained within the sample to fluoresce. Fluorescence 336 is detected by individual photodetectors 338*a*, 338*b*, and 338*c*. Filters 450 captures the desired wavelengths for each of the individual photodetectors.

Control/data acquisition/data processing circuitry 108 (FIG. 1) controls much of the operation of interrogation cell 106. In this context, this circuitry, which in some embodiments includes a processor and memory, is capable of:

driving LED(s) 332; and
capable of intermittently pulsing LED(s) 332; and
enabling photodetector(s) 338.

Photodetector 338 generates a signal(s) in known fashion when it receives fluorescent emissions 336. In some embodiments, the signal(s) is indicative of the wavelength(s) of the fluorescent emissions and the intensity of those emissions.

Control/data-acquisition/data-processing circuitry 108 receives the signal(s) from the photodetector (representative of the fluorescent emissions) and performs one or more of the following tasks:

stores a representation of the signal; and/or
partially processes the signal; and/or
fully processes the signal; and/or
transmits (in conjunction with transmitter 114), to central station 116:
   a representation of the signal; or
   a representation of the signal as well as data obtained from partially processing the signal; or
   a representation of the signal as well as data obtained from fully processing the signal; or
   only the information obtained from processing the signal.

In some embodiments, operation 208 (i.e., monitoring the collection media for fluorescent emissions) also includes the task(s) described above.

As indicated above, in some embodiments, at least some processing of the signal(s) from photodetector 338 is performed at central station 116. Doing so facilitates using additional, more powerful data-processing algorithms to analyze the information contained in the signals.

The information obtained from the signal(s) from photodetector 338 can be used to:

detect biological agents;
estimate the amount of biological agent detected;
determine if the amount of biological agent present is indicative of a biological attack or otherwise poses a risk to the health of the local population, livestock, etc.;
identify the biological agents that are detected.

As to detection, the detection of fluorescence, particularly at certain wavelengths, might be indicative of the presence of a biological agent. The intensity of the signal, as well as the air flow through the interrogation cell and the amount of time that the air has been flowing provides information related to the amount of biological agent present in the environment. In other words, it can be used to develop a particulate count as a function of wavelength. As to identification, the wavelength of fluorescent emissions measured by interrogation cell 106 can be compared to the wavelength of fluorescent emissions of known biological agents. Correspondence between the measured emissions and one of the references is indicative of the presence of that biological agent. For further information about identification of biological agents, see applicants co-pending U.S. patent application Ser. No. 10/891,573.

In the illustrative embodiment, the results of signal processing are presented via a graphical user interface. In the embodiment that is depicted in FIG. 9, graphical user interface 962 displays the data as an "intensity" or "particle count" as a function of frequency, $f_i$, (or wavelength, $\lambda_i$) of the fluorescent emissions. In some embodiments, an alarm limit, $AL_i$, is displayed for each "type" (i.e., each different frequency or wavelength) of biological agent. In the illustrative embodiment, when an alarm limit $AL_i$ is exceeded, an alarm indication 964 (e.g., sound, flashing light, etc.) is provided.

In the embodiment that is depicted in FIG. 10, graphical user interface 1066 provides particle count/intensity as a function of frequency/wavelength and time.

Sensing system 100 can be used in a variety of applications. For example, it can be deployed in a subway station. For such an application, sensing system 100 samples (either periodically or constantly) the ambient air. Information that is obtained from interrogation of particulates within the air sample is transmitted (either in raw form or after some signal processing), via a transmitter, to a central office or station. Particulate levels are continuously monitored and displayed, such as via graphical user interfaces 962 or 1064.

It is to be understood that the above-described embodiments are merely illustrative of the present invention and that many variations of the above-described embodiments can be devised by those skilled in the art without departing from the scope of the invention. For example, in this Specification, numerous specific details are provided in order provide a thorough description and understanding of the illustrative embodiments of the present invention. Those skilled in the art will recognize, however, that the invention can be practiced without one or more of those details, or with other methods, materials, components, etc. In particular, as appropriate, features that are disclosed in co-pending U.S. patent application Ser. Nos. 10/891,805, 10/891,812, 10/891,573, and 10/891,638 can be used in conjunction with the illustrative embodiment that is depicted and described herein. Those skilled in the art will know how to integrate such features into the illustrative embodiment of the present invention.

In some instances, well-known structures, materials, or operations are not shown or described in detail to avoid obscuring aspects of the illustrative embodiments. It is understood that the various embodiments shown in the Figures are illustrative, and are not necessarily drawn to scale. Reference throughout the specification to "one embodiment" or "an embodiment" or "some embodiments" means that a particular feature, structure, material, or characteristic described in connection with the embodiment(s) is included in at least one embodiment of the present invention, but not necessarily all embodiments. Consequently, the appearances of the phrase "in one embodiment," "in an embodiment," or "in some embodiments" in various places throughout the Specification are not necessarily all referring to the same embodiment. Furthermore, the particular features, structures, materials, or characteristics can be combined in any suitable manner in one or more embodiments. It is therefore intended that such variations be included within the scope of the following claims and their equivalents.

We claim:

1. An apparatus for the detection of biological agents, wherein said apparatus comprises an interrogation cell, said interrogation cell having:
    a stationary phase collection media for collecting a sample;
    a source of electromagnetic radiation for intermittently exposing said sample to electromagnetic radiation;
    a photodetector for detecting fluorescent emissions from biological agents that are contained in said sample resulting from the illumination; and
    a device purging at least a portion of said sample from said collection media.

2. The apparatus of claim 1 wherein said collection media comprises PTFE.

3. The apparatus of claim 2 wherein said collection media is selected from the group consisting of PTFE, PFA and PFE.

4. The apparatus of claim 1 wherein said collection media traps at least about 99 percent of particulates having a size of 0.3 microns.

5. The apparatus of claim 1 wherein said source of radiation is a light-emitting diode.

6. The apparatus of claim 5 wherein said light-emitting diode is disposed out-of-plane at an angle in a range of about 45 to 60 degrees relative to said collection media.

7. The apparatus of claim 1 further comprising control/data-acquisition/data-processing circuitry, wherein:
    said source of electromagnetic radiation and said photodetector are electrically coupled to said control/data-acquisition/data-processing circuitry; and
    said control/data-acquisition/data-processing circuitry controls the operation of said source of electromagnetic radiation and the operation of said photodetector.

8. The apparatus of claim 1 further comprising:
    a cell inlet line, wherein said inlet line directs air to said collection media; and
    a cell outlet line, wherein said cell outlet line exhausts air that has passed through said collection media.

9. The apparatus of claim 7 further comprising a filter, wherein said filter is disposed upstream of said cell inlet line, and wherein said filter removes particles larger than about 50 microns from said air being directed to said collection media.

10. The apparatus of claim 1 wherein said device for purging comprises a pump.

11. The apparatus of claim 1 wherein said source of electromagnetic radiation has a peak emission wavelength within a range of wavelengths from about 250 to about 500 nanometers.

12. An apparatus for the detection of biological agents comprising:
    collection media for collecting a sample, wherein said sample comprises a plurality of particulates;
    a light-emitting diode, wherein said light-emitting diode is arranged to expose said sample to electromagnetic radiation;
    circuitry for intermittently activating said light-emitting-diode;
    a photodetector for detecting fluorescence, wherein said fluorescence originates from at least some of said particulates that are biological agents;
    a device for purging at least a portion of said sample from said collection media; and
    circuitry for calculating a total amount of fluorescence occurring at a first wavelength, wherein said total amount of fluorescence relates to a quantity of a first type of particulates fluorescing at said first wavelength.

* * * * *